US006730062B2

(12) United States Patent
Hoffman et al.

(10) Patent No.: US 6,730,062 B2
(45) Date of Patent: May 4, 2004

(54) SAFETY CATHETER WITH NON-REMOVABLE RETRACTABLE NEEDLE

(75) Inventors: Douglas B. Hoffman, Harrison, OH (US); Ananth R. Krishnan, Arlington, TX (US)

(73) Assignee: Medex, Inc., Carlsbad, CA (US)

( * ) Notice: Subject to any disclaimer, the term of this patent is extended or adjusted under 35 U.S.C. 154(b) by 0 days.

(21) Appl. No.: 09/975,373

(22) Filed: Oct. 11, 2001

(65) Prior Publication Data

US 2003/0073956 A1 Apr. 17, 2003

(51) Int. Cl.[7] ............................................. A61M 5/178
(52) U.S. Cl. .............................. 604/164.02; 604/164.02
(58) Field of Search ............................... 604/6.05, 6.06, 604/19, 506, 507, 513, 93.01, 110, 158–170, 264, 240, 239, 533, 93.1; 128/919

(56) References Cited

U.S. PATENT DOCUMENTS

| | | | |
|---|---|---|---|
| 5,137,515 A | * | 8/1992 | Hogan ........................ 604/110 |
| 5,665,072 A | * | 9/1997 | Yoon ...................... 604/164.12 |
| 5,685,863 A | * | 11/1997 | Botich et al. ............... 604/198 |
| 6,077,244 A | | 6/2000 | Botich et al. |
| 6,126,641 A | * | 10/2000 | Shields ........................ 604/192 |

FOREIGN PATENT DOCUMENTS

| | | |
|---|---|---|
| WO | 99/08742 A1 | 2/1999 |
| WO | 99/24092 A1 | 5/1999 |
| WO | 00/06221 A1 | 2/2000 |
| WO | 00/57940 A1 | 10/2000 |

* cited by examiner

Primary Examiner—LoAn H. Thanh
(74) Attorney, Agent, or Firm—Wood, Herron & Evans, LLP

(57) ABSTRACT

A safety introducer for insertion into a vessel of a patient for infusion of fluids into or withdraw of fluids from the vessel. The introducer includes a catheter assembly having a catheter tube attached to a catheter body. The catheter body has an elongated cavity extending therethrough which is in fluid communication with the catheter tube. The introducer further includes a needle assembly having an elongated needle attached to a flexible tube. The flexible tube is in fluid communication with the elongated cavity. The needle assembly is slidably disposed within the elongated cavity such that a proximally directed force exerted on the flexible tube withdraws the needle assembly substantially completely within the elongated cavity.

6 Claims, 8 Drawing Sheets

SAFETY CATHETER WITH NON-REMOVABLE RETRACTABLE NEEDLE

FIELD OF THE INVENTION

This invention generally relates to intravenous (IV) catheters; and more particularly, the invention relates to a safety catheter with a retractable needle fixed to the catheter.

BACKGROUND OF THE INVENTION

An intravenous (IV) catheter is an instrument that is used to introduce certain fluids such as saline solution directly into the bloodstream of a patient. Typically, a needle or other stylet is first introduced through the cannula portion of the catheter and into the skin of the patient at the desired location such as the back of the patient's hand or a vessel on the inside of the arm. Once insertion is complete, the needle is removed from the cannula portion of the catheter. After removing the needle, a fluid handling device such as a syringe or IV bag is attached to the luer fitting located at the proximal end of the catheter hub. Fluid is then infused directly from the fluid handling device through the catheter into the bloodstream of the patient.

When the needle is removed from the cannula, the health care worker must place the exposed needle tip at a nearby disposal unit while simultaneously addressing the task required to infuse the fluids into the patient. It is at this juncture that the exposed needle tip creates a danger of an accidental needle stick occurring which leaves the health care worker vulnerable to the transmission of various, dangerous blood-borne pathogens such as human immune virus (HIV) and hepatitis. The risk of a contaminated needle stick is not just isolated to the health care worker inserting the intravenous catheter. Careless disposal of used needles can put other health care workers at risk as well. Even others outside the health care profession, for example those involved in the clean-up and final disposal of medical waste can be at risk of an accidental needle stick from a carelessly discarded needle.

The danger to health care workers and others outside the health care profession from accidental needle sticks has yielded the development of catheters with safety mechanisms in which the occurrence of such accidental needle sticks is prevented. An example of a catheter having a safety mechanism is disclosed in U.S. Pat. No. 6,077,244 issued to Botich et al. on Jun. 20, 2000. A catheter insertion device is described in which the needle is retracted within the housing of the device after use to prevent contaminated needle exposure. A needle retainer releasably retains the needle in an extended position against the rearward bias of the biasing element. The needle retainer engages the hub of the catheter so that when the catheter is removed from the insertion device, the needle retainer automatically releases the needle. The biasing element then propels the needle rearwardly into the housing of the device. The housing can then be safely removed from the catheter enabling a fluid handling device to be attached to the catheter hub.

The advancement of such safety mechanisms on catheters have reduced concerns associated with inadvertent needle sticks; however, there is still opportunity for improvement. The catheters in the prior art have safety mechanisms which shield the needle tip during removal from the catheter to prevent inadvertent needle sticks. Even though the needle tip is shielded, there is still a risk of an accidental needle stick to health care workers or others outside the health care profession. For example, a needle might not retract entirely into its shield or housing. After the needle is removed from the catheter, the tip would be exposed creating a risk of an accidental needle stick. In addition, the safety mechanisms on the catheters in the prior art were not developed to eliminate the risk of exposure to bodily fluids. For example, when the health care worker removes the needle from the catheter, the tip even though safety shielded might discharge some bodily fluids on his gloves. The health care worker could then proceed to inadvertently touch his eye while still wearing the gloves creating a risk of infection from the discharged bodily fluid. In addition, safety catheters of the type mentioned above require the health care worker to separately dispose of the needle and the catheter, thereby providing for two instances where the health care worker is at risk.

Therefore, there has been a desire for an improved catheter which reduces the risk of an inadvertent needle stick and bodily fluid exposure.

SUMMARY OF THE INVENTION

In accordance with the present invention there is provided a safety introducer for insertion into a vessel of a patient for infusion of fluids into or withdraw of fluids from the vessel. The introducer includes a catheter assembly with an elongated catheter tube having lumen extending from a distal end to a proximal end. The proximal end of the tube is attached to a distal end of a catheter body. The catheter body has an elongated cavity extending therethrough from the distal end to a proximal end. The cavity is in fluid communication with the catheter tube. The introducer further includes a needle assembly with an elongated needle having a lumen extending from a distal end to a proximal end. The proximal end of the needle is attached to a distal end of a flexible tube. The flexible tube has a lumen extending from the distal end to a proximal end which is in fluid communication with the elongated cavity. The needle assembly being slidably disposed within the elongated cavity such that a proximally directed force exerted on the flexible tube withdraws the needle assembly substantially completely within the elongated cavity.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

DETAILED DESCRIPTION OF THE INVENTION

As used in this description, "proximal" or "proximally" refers to that portion of the instrument, component, or element which extends toward the user. Conversely, "distal" or "distally" refers to that portion of the instrument, component, or element which extends away from the user.

Figure 1:
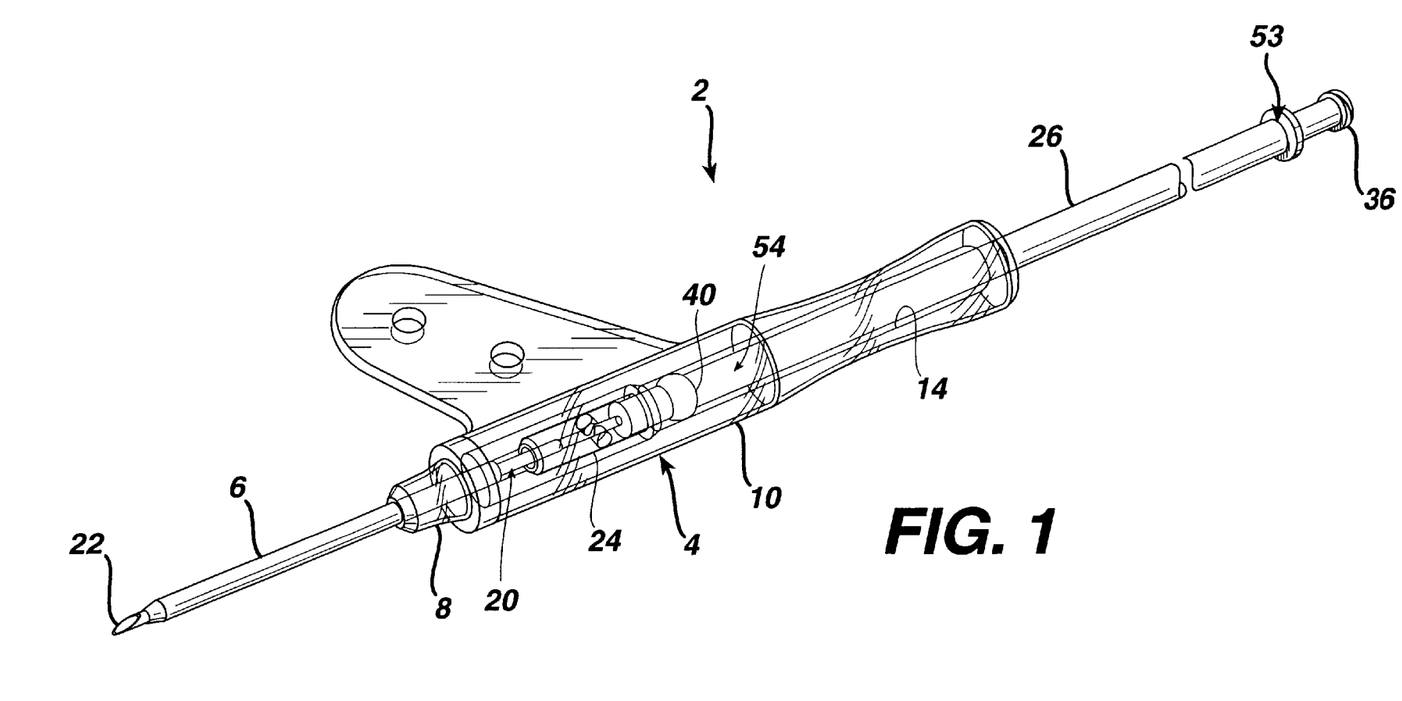
FIG. 1 is a perspective view of a intravenous assembly including the catheter assembly and needle assembly of the present invention.
Figure 2:
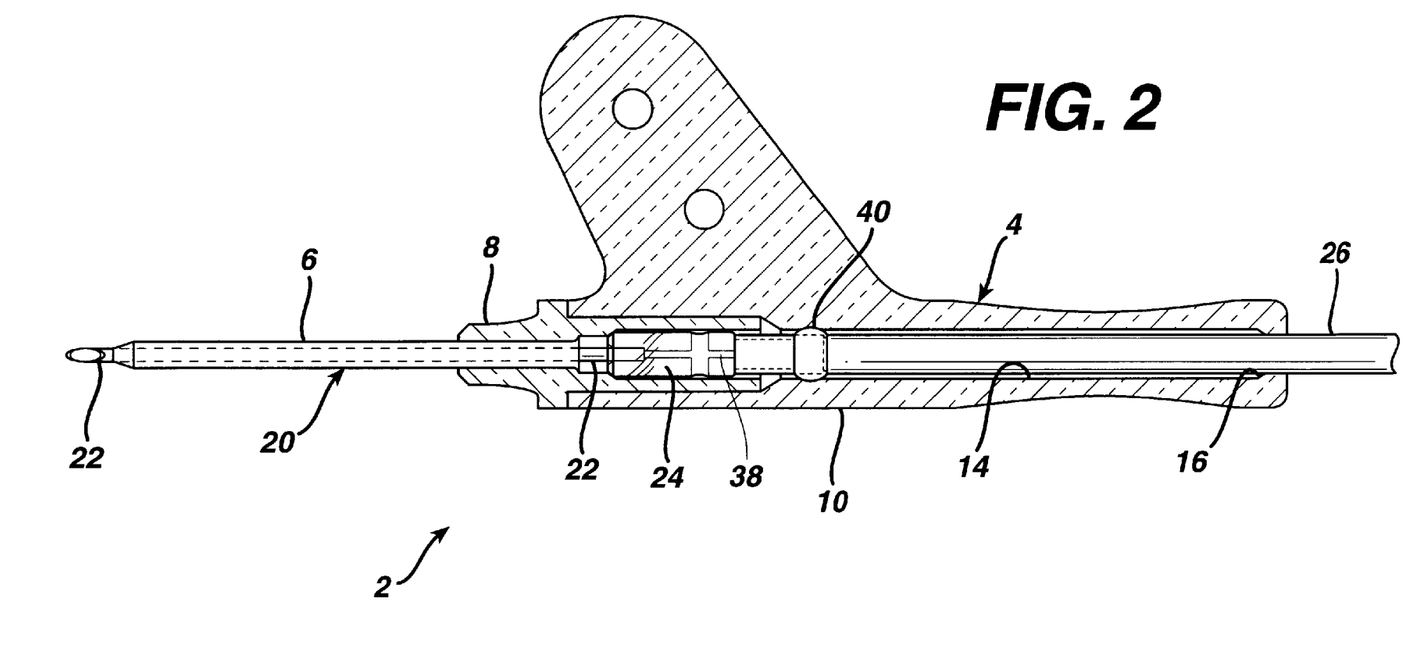
FIG. 2 is a cross-sectional view along 2—2 of FIG. 1 of the intravenous assembly showing the needle exposed distally from the catheter.
Figure 3:
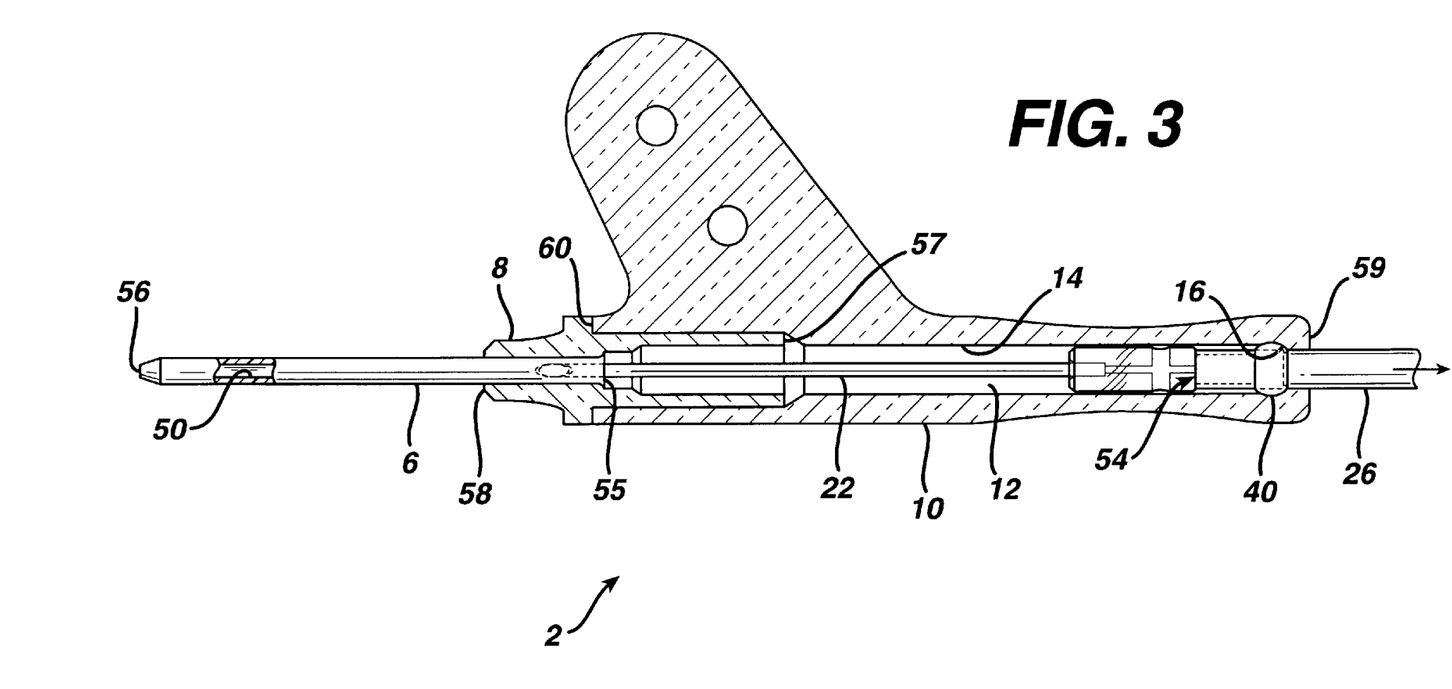
FIG. 3 is a cross-sectional view similar to FIG. 2 of the intravenous assembly showing the needle retracted within the catheter body.
Figure 4:
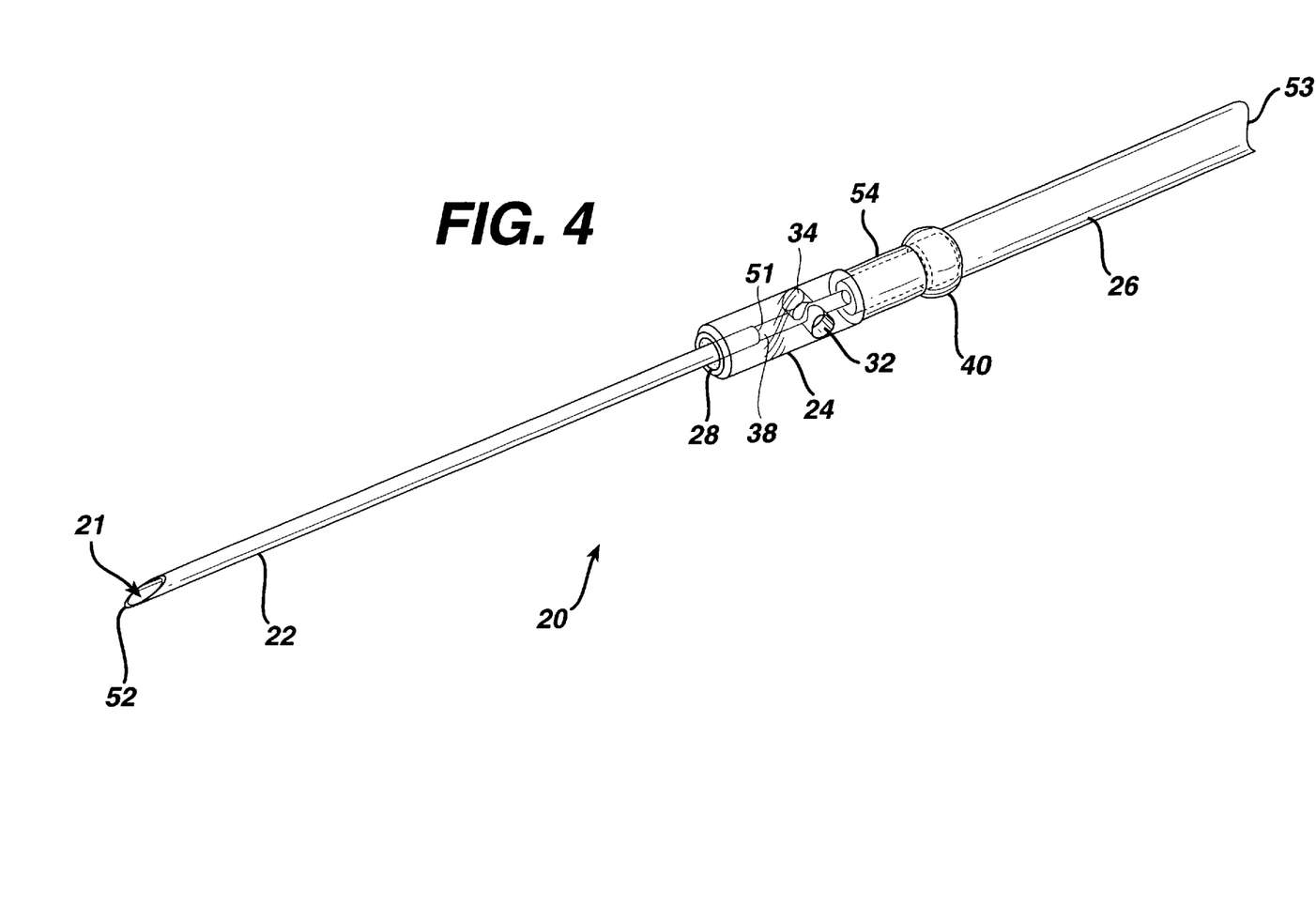
FIG. 4 is perspective view of the needle assembly of the present invention.
Figure 5:
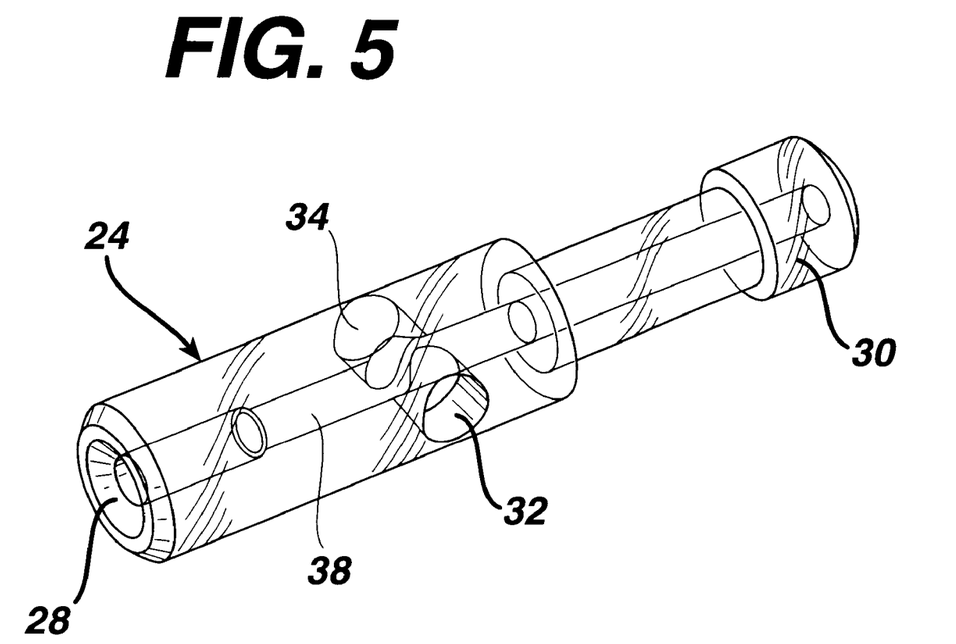
FIG. 5 is perspective view of the coupler of the needle assembly of the present invention.
Figure 6:
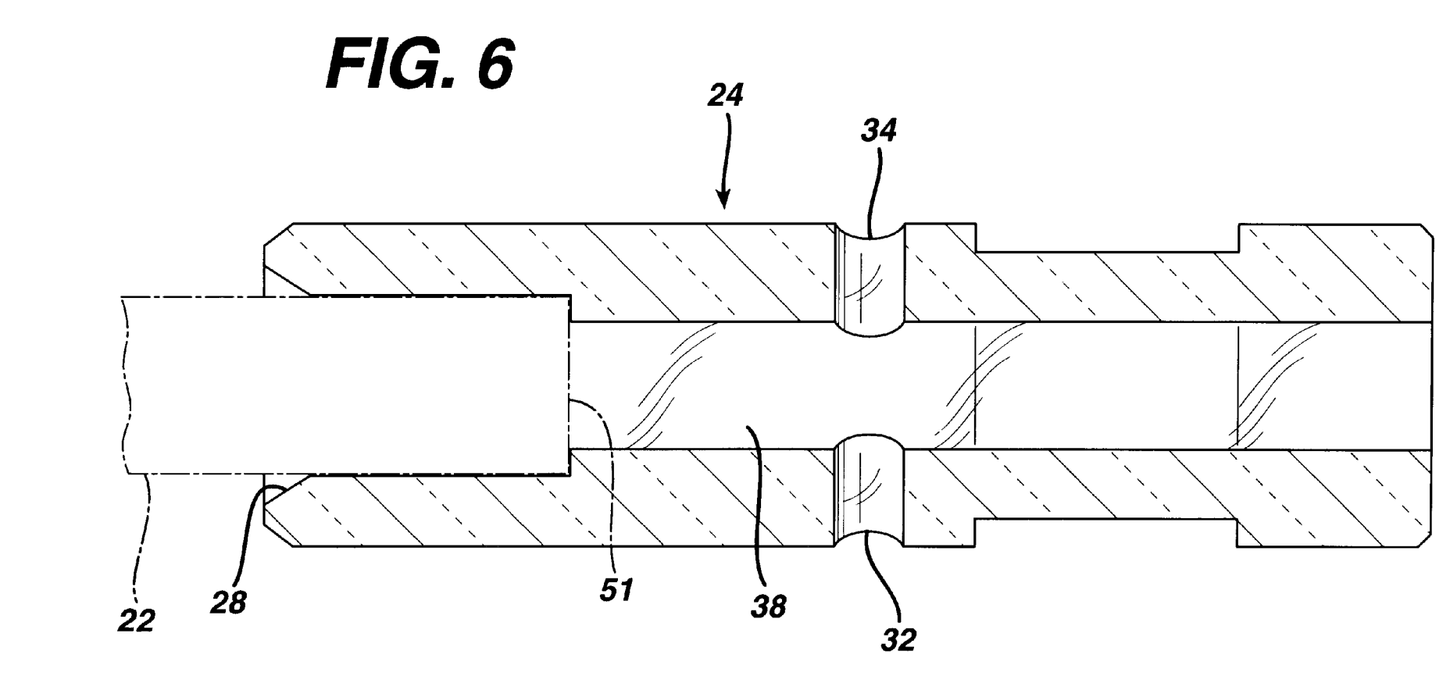
FIG. 6 is a cross-sectional view taken along line 4—4 of the coupler of the present invention.

Referring to FIGS. 1, 2, and 3, IV assembly, or safety introducer, 2 of the present invention includes catheter assembly 4 and needle assembly 20. Needle assembly 20 includes needle 22 and coupler 24. As illustrated in FIG. 4, needle 22, which is preferably made of stainless steel, is generally an elongated tubular structure with proximal end 51 and distal end 52. Proximal end 51 of needle 22 is fixedly attached to glue well 28 on the distal end of coupler 24. Coupler 24 which is preferably made of a translucent or transparent polymer such as, for example, polycarbonate, is generally a tubular structure having coupler cavity 38 in fluid communication with lumen 21 of needle 22. Coupler 24 further comprises side ports 32 and 34 and bullet end 30 (shown in FIG. 5). As illustrated in FIGS. 5 and 6, side ports 32 and 34 are openings normal to the axis of coupler 24 which allow fluid to pass therethrough. Side ports 32 and 34 are in fluid communication with coupler cavity 38

Referring back now to FIGS. 1 and 2, needle assembly 20 further comprises tube 26 and a sealing member, or tube bulge, 40. Tube 26 is preferably made of a flexible PVC, but can be made from any number of materials known to those skilled in the art. Tube 26 is generally a tubular structure having proximal end 53 and distal end 54. Proximal end 53 of tube 26 is fixedly attached to luer fitting 36. Luer fitting 36, well known in the medical art, provides for secure, leak proof attachment of tubing, syringes, or many other medical devices used to infuse or withdraw fluids through IV assembly 2. Distal end 54 of tube 26 is inserted over bullet end 30 (see FIG. 5) of coupler 24 creating tube bulge 40. Tube bulge 40 is generally a semi spherical structure, which is described in more detail later.

Referring again to FIGS. 2 and 3, catheter assembly 4 includes an elongated catheter tube 6 which is a tubular structure having proximal end 55 and a distal end 56, and a lumen 50 extending therebetween. Catheter 6 could be comprised of many suitable materials known in the art most of which are flexible thermoplastics such as, for example, polyurethane. Catheter cap 8 is generally a conical structure having proximal end 57 and distal end 58. Distal end 58 of catheter cap 8, which has an opening therethrough, is fixedly attached to proximal end 55 of catheter 6. Catheter cap 8 may be made from a suitable, rigid polymer such as, for example, polypropylene. Catheter assembly 4 further includes catheter body 10, which is preferably made of a translucent or transparent polymer such as, for example, polycarbonate. Catheter body 10 is generally a tubular structure with body cavity 12 therethrough having proximal end 59 and distal end 60. Distal end 60 of catheter body 10 is fixedly attached to proximal end 57 of catheter cap 8.

Prior to attaching catheter body 10 and catheter cap 8, needle 22 is inserted through catheter cap 8 and catheter 6 extending distally therefrom. Distal end 60 of catheter body 10 is then slipped over proximal end 53 of tube 26. Catheter body 10 is then advanced toward the distal end of needle assembly 20. Sliding catheter body 10 over tube bulge 40 creates a seal fit which prevents fluids from escaping through proximal end 59 of catheter body 10 and creates a frictional fit with body cavity walls 14 and 16 which limits the travel of needle assembly 20. After advancement is complete, distal end 60 of catheter body 10 is attached to proximal end 57 of catheter cap 8, which has needle 22 therethrough. Luer fitting 36 is then attached to proximal end 53 of tube 26.

In an actual intravenous insertion procedure utilizing the device of the present invention, a health care worker positions IV assembly 2 at the desired location. The health care worker then proceeds to apply pressure on IV assembly 2 causing needle 22, which extends distally from catheter 6 to pierce the skin of the patient. Continuing to apply pressure, the health care worker advances IV assembly 2 distally into the vein of the patient. During advancement, needle 22 creates a hole allowing catheter 6 to be inserted into the vein. After insertion is complete, the health care worker pulls on proximal end 53 of tube 26 which retracts needle 22 from catheter 6 into catheter body 10 and catheter cap 8 of IV assembly 2, as shown in FIG. 3. While needle 22 is retracted into catheter body 10 and catheter cap 8, blood may flow up into body cavity 12 of catheter body 10, but the fit between body cavity wall 14 and tube bulge 40 creates a seal which does not allow the blood to escape out of the proximal end of IV assembly 2. Tube 26 is pulled until tube bulge 40 stops against proximal cavity wall 16 of catheter body 10. A fluid handling device such as, for example, a syringe can then be attached to luer fitting 36 to proximal end 53 of tube 26. Fluid then flows directly from the fluid handling device through tube 26, coupler 24, needle 22, and catheter 6 into the bloodstream of the patient. Some of the fluid will pass out side ports 32 and 34 of coupler 24 washing any residual blood back into the vein not allowing it to sit and become stagnate.

As seen from the above description, the present invention has many advantages over prior art safety catheters. A guidewire is not needed to retract the needle. Instead, the flexible tube retracts the needle. This design allows for a reduced number of parts, as the guidewire can be eliminated. Because the needle assembly is not separated from the catheter assembly at the time of insertion, there is only one single unit to dispose of when the product is finished.

Figure 7:
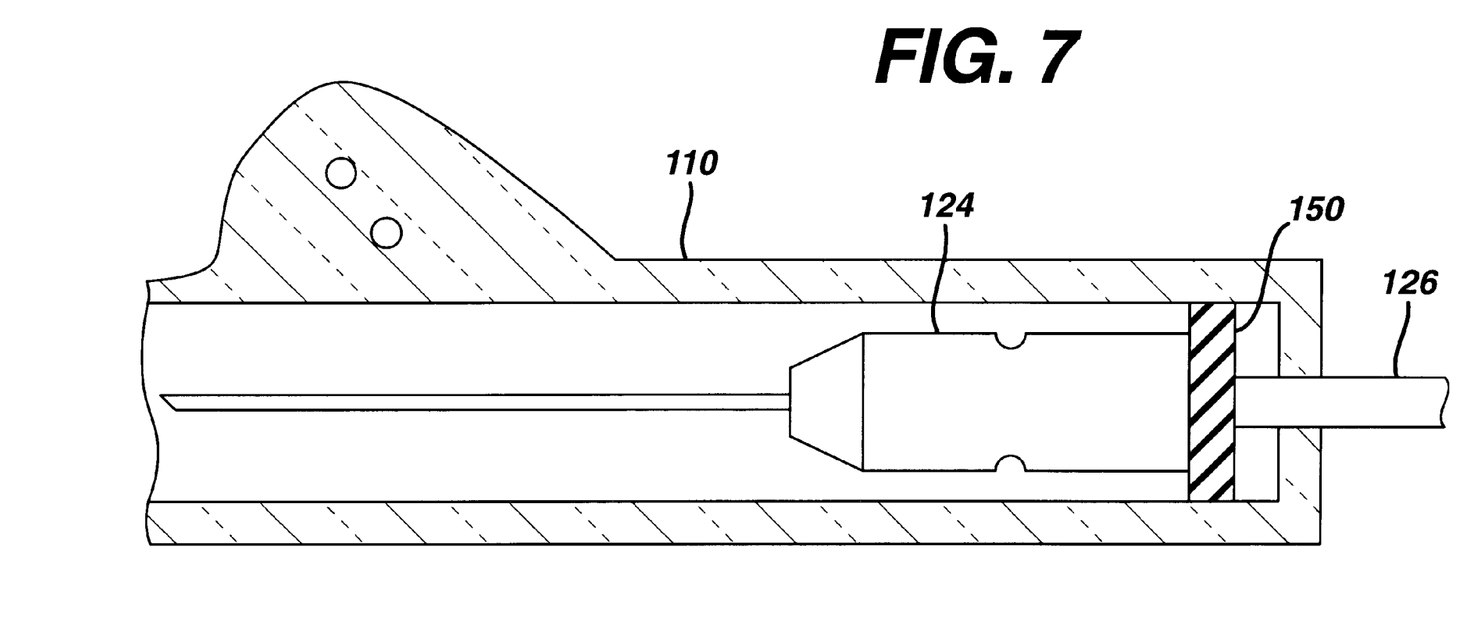
FIG. 7 is a cross-sectional view of an alternate embodiment of the present invention.

An alternate embodiment of the present invention is shown in FIG. 7. In this embodiment, coupler 124, similar to coupler 24, includes seal 150 attached to the distal end of coupler 124. Seal 150 replaces tube bulge 40 in the preferred embodiment. Seal 150 is generally a doughnut shape made of a material such as, for example, silicone or any other flexible material known to those skilled in the art. Attached to the distal end of coupler 124, seal 150 completely surrounds tube 126 preventing fluids from escaping catheter body 110.

Figure 8:
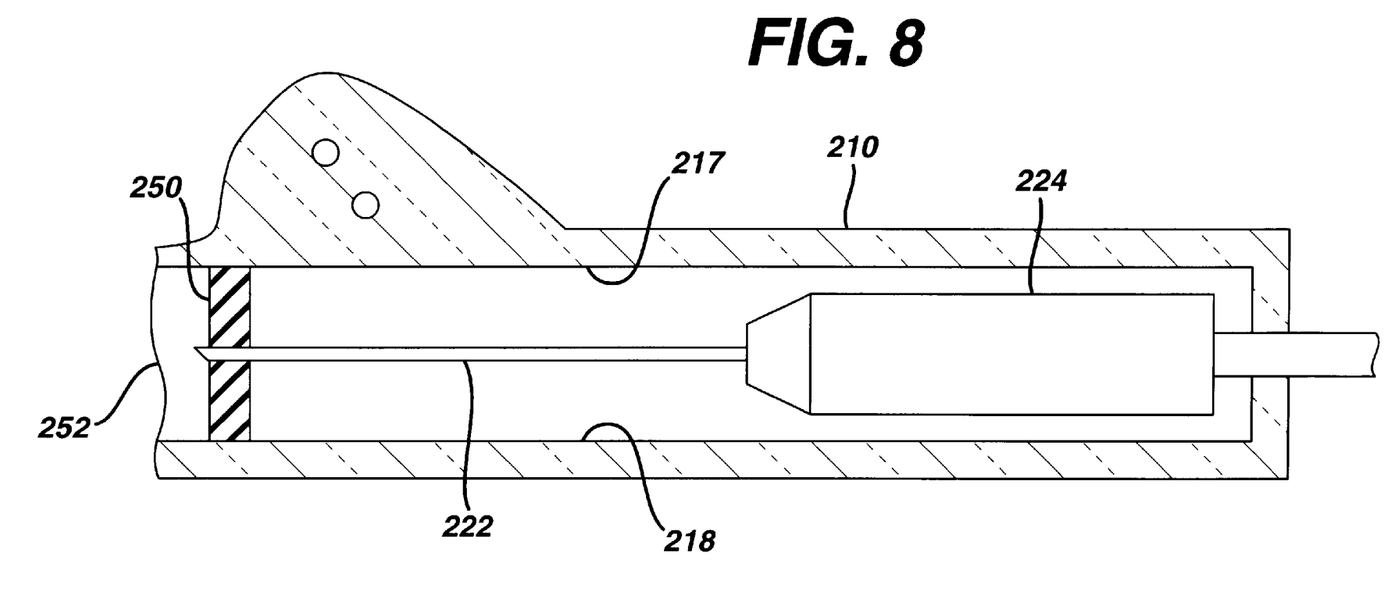
FIG. 8 is a cross-sectional view of another alternate embodiment of the present invention.

FIG. 8 shows another alternate embodiment where coupler 224, similar to coupler 124, includes seal 250. Seal 250 which functions to replace tube bulge 40 in the preferred embodiment is fixedly attached to distal cavity walls 217 and 218 of catheter body 210. Seal 250 is generally a doughnut shape made of a material such as, for example, silicone or any other flexible material known to those skilled in the art. Completely surrounding distal end 252 of needle 222, seal 250 prevents fluids from escaping catheter body 210.

While preferred embodiments of the present invention have been shown and described herein, it will be obvious to those skilled in the art that such embodiments are provided by way of example only. In addition, for each structure mentioned above, it should be understood that such structure can be described or characterized as a means for performing its intended function. Numerous variations, changes, and substitutions will now occur to those skilled in the art without departing from the invention. Accordingly, it is intended that the invention be limited only by the spirit and scope of the appended claims.

What is claimed:

1. A safety introducer for insertion into a vessel of a patient for infusion of fluids into or withdraw of fluids from the vessel, said introducer comprising:

a) a catheter assembly including an elongated catheter tube having a lumen extending from a distal end of said tube to a proximal end of said tube, said proximal end of said tube is attached to a distal end of a catheter body, said catheter body having an elongated cavity extending therethrough from a distal end of said catheter body to a proximal end of said catheter body, said cavity is in fluid communication with said catheter tube; and b) a needle assembly including an elongated needle having a lumen extending from a distal end of said needle to a proximal end of said needle, a flexible tube having a distal end fixedly connected to said needle assembly and a lumen extending from said distal end of said flexible tube to a proximal end of said flexible tube extending outside of said elongated cavity and which is in fluid communication with said elongated cavity, said needle assembly being slidably disposed within said elongated cavity such that a proximally directed force exerted on said flexible tube moves said flexible tube proximally and withdraws said needle assembly substantially completely within said elongated cavity, wherein said needle assembly further includes a coupler for attaching and disposed between said needle to said flexible tube, said coupler including at least one radial side port for allowing fluid to flow from said flexible tube, out through said ports and around said needle.

2. The introducer of claim 1 wherein said proximal end of said flexible tube includes a fitting for attaching said flexible tube to other medical devices.

3. A safety introducer for insertion into a vessel of a patient for infusion of fluids into or withdraw of fluids from the vessel, said introducer comprising:

a. a catheter assembly including an elongated catheter tube having a lumen extending from a distal end of said catheter tube to a proximal end of said tube, said proximal end of said tube is attached to a distal end of a catheter body, said catheter body having an elongated cavity extending therethrough from a distal end of said catheter body to a proximal end of said catheter body, said cavity is in fluid communication with said catheter tube; and b. a needle assembly including an elongated needle having a lumen extending from a distal end of said needle to a proximal end of said needle, a flexible tube having a distal end connected to said needle assembly and a lumen extending from said distal end of said flexible tube to a proximal end of said flexible tube extending outside of said elongated cavity and which is in fluid communication with said elongated cavity, said needle assembly being slidably disposed within said elongated cavity such that a proximally directed force exerted on said flexible tube moves said flexible tube proximally and withdraws said needle assembly substantially completely within said elongated cavity, said needle assembly further includes a sealing member disposed within said elongated cavity to prevent fluid from flowing around said flexible tube and out through said proximal end of said catheter body.

4. The introducer of claim 3 wherein said sealing member is proximate to said distal end of said flexible tube.

5. The introducer of claim 3 wherein said needle assembly further includes a coupler for attaching and disposed between said needle to said flexible tube, said coupler including at least one radial side port for allowing fluid to flow from said flexible tube, out through said ports and around said needle.

6. The introducer of claim 3 wherein said proximal end of said flexible tube includes a fitting for attaching said flexible tube to other medical devices.

* * * * *

UNITED STATES PATENT AND TRADEMARK OFFICE
CERTIFICATE OF CORRECTION

PATENT NO. : 6,730,062 B2
DATED : May 4, 2004
INVENTOR(S) : Douglas B. Hoffman et al.

It is certified that error appears in the above-identified patent and that said Letters Patent is hereby corrected as shown below:

Title page,
Item [57], ABSTRACT,
Line 2, "withdraw of fluids" should read -- withdrawal of fluids --

Column 1,
Line 60, "have reduced" should read -- has reduced --

Column 2,
Line 23, "withdraw of fluids" should read -- withdrawal of fluids --
Line 53, "view along 2-2 of FIG. 1" should read -- view along line 2-2 of FIG. 1 --
Line 60, "FIG. 4 is perspective view of" should read -- FIG. 4 is a perspective view of --
Line 62, "FIG. 5 is perspective view of" should read -- FIG. 5 is a perspective view of --

Column 3,
Line 28, "cavity 38" should read -- cavity 38. --
Line 41, "semi spherical" should read -- semi-spherical --

Column 5,
Line 10, "withdraw of fluids" should read -- withdrawal of fluids --

Column 6,
Line 2, "withdraw of fluids" should read -- withdrawal of fluids --

Signed and Sealed this

Thirteenth Day of July, 2004

JON W. DUDAS
*Acting Director of the United States Patent and Trademark Office*